United States Patent [19]

Sofranko

[11] Patent Number: 4,517,398

[45] Date of Patent: May 14, 1985

[54] HYDROXYLATED MAGNESIA SUPPORT

[75] Inventor: John A. Sofranko, Malvern, Pa.

[73] Assignee: Atlantic Richfield Company, Los Angeles, Calif.

[21] Appl. No.: 600,940

[22] Filed: Apr. 16, 1984

[51] Int. Cl.³ .................................................. C07C 2/00
[52] U.S. Cl. ..................................... 585/500; 585/417; 585/400; 585/541; 585/654; 585/658; 585/700; 585/943
[58] Field of Search ............... 585/415, 400, 417, 418, 585/500, 541, 654, 656, 658, 661, 943, 700

[56] References Cited

U.S. PATENT DOCUMENTS

| | | | |
|---|---|---|---|
| 4,205,194 | 5/1980 | Mitchell et al. | 585/500 |
| 4,239,658 | 12/1980 | Mitchell et al. | 585/500 |
| 4,443,645 | 4/1984 | Jones et al. | 585/500 |
| 4,443,648 | 4/1984 | Jones et al. | 585/500 |

OTHER PUBLICATIONS

Keller, G. E., "Syntheses of Ethylene via Oxidative Coupling of Methane," J. of Catalysis, 73, 9–19/1982.

*Primary Examiner*—Delbert E. Gantz
*Assistant Examiner*—Cynthia A. Prezlock
*Attorney, Agent, or Firm*—Craig E. Larson

[57] ABSTRACT

A method for converting methane to higher hydrocarbon products by contacting, at conditions to convert said hydrocarbons, at least one reducible oxide of at least one metal, associated with a hydroxylated magnesia support (that is, magnesia derived from magnesium hydroxide or a magnesium-containing component contacted with hydroxyl-containing material), which support is calcined prior to the addition of the reducible oxide.

15 Claims, No Drawings

HYDROXYLATED MAGNESIA SUPPORT

BACKGROUND OF THE INVENTION

1. Field of the Invention

This invention relates to the synthesis of hydrocarbons from a methane source. A particular application of this invention is a method for converting natural gas to more readily transportable material using a methane conversion catalyst supported by hydroxylated magnesia.

2. Description of the Pertinent Art

A major source of methane is natural gas. Other sources of methane have been considered for fuel supply (e.g., the methane present in coal deposits or formed during mining operations). Relatively small amounts of methane are also produced in various petroleum processes.

The composition of natural gas at the wellhead varies, but the major hydrocarbon present is methane. For example, the methane content of natural gas may vary within the range of about 40 to about 95 volume percent. Other constituents of natural gas include ethane, propane, butane, pentane (and heavier hydrocarbons), hydrogen sulfide, carbon dioxide, helium, and nitrogen.

Natural gas is classified as dry or wet, depending upon the amount of condensable hydrocarbons contained in it. Condensable hydrocarbons generally comprise $C_3+$ hydrocarbons, although some ethane may be included. Gas conditioning is required to alter the composition of wellhead gas; processing facilities usually being located in or near the production fields. Conventional processing of wellhead natural gas yeilds processed natural gas containing at least a major amount of methane.

Large-scale use of natural gas often requires a sophisticated and extensive pipeline system. Liquefaction has also been employed as a transportation means, but processes for liquefying, transporting and revaporizing natural gas are complex, energy intensive and require extensive safety precautions. Transport of natural gas has been a continuing problem in the exploitation of natural gas resources. It would be extremely valuable to be able to convert methane (e.g., natural gas) to more readily transportable products. Moreover, direct conversion to olefins such as ethylene or propylene would be extremely valuable to the chemical industry.

Recently, it has been discovered that methane may be converted to higher hydrocarbons by a process which comprises contacting methane with an oxidative synthesizing agent at synthesizing conditions (e.g., at a temperature selected within the range of about 500° to about 1000° C.). An oxidative synthesizing agent is a composition having as a principal component at least one oxide of at least one metal, which composition produces higher $C_2+$ hydrocarbon products, water, and a composition comprising a reduced metal oxide when contacted with methane. Reducible oxides of several metals have been identified which are capable of converting methane to higher hydrocarbons. In particular, oxides of manganese, tin, indium, germanium, lead, antimony and bismuth are most useful.

Accordingly, an object of this invention is to provide an improved process for converting methane to higher hydrocarbons. A further object of this invention is an improved oxidative synthesizing agent-one capable of converting methane with reduced byproduct selectivities. A still further object of the present invention is an oxidative synthesizing agent with improved stability-an agent that maintains desirable conversion properties for longer periods of time.

Other aspects, objects and the several advantages of this invention will become apparent to those skilled in the art upon reading this Specification and the appended claims.

SUMMARY OF THE INVENTION

An improved hydrocarbon conversion process has been discovered which comprises contacting hydrocarbons, preferably a gas comprising methane, with a contact agent at conditions to convert the hydrocarbons, preferably at a temperature selected within the range of about 300° to about 1200° C., more preferably about 500° to about 1000° C., which agent comprises:

(a) at least one reducible oxide of at least one metal, which oxide(s) are reduced and produce higher hydrocarbon products and water when contacted with methane at selected temperatures, preferably in the range of about 500° to about 1000° C.; and (b) a support comprising hydroxylated magnesia, which support is calcined prior to addition of at least one metal, the oxide of which is reducible.

The term "hydroxylated magnesia" means a magnesia derived from magnesium hydroxide or a magnesium-containing component contacted with hydroxyl-containing material.

DETAILED DESCRIPTION OF THE INVENTION

The contact agent of this invention is a composition comprising at least one reducible oxide of at least one metal and a hydroxylated magnesia support. The reducible oxide produces higher hydrocarbon products, water and a reduced metal oxide when contacted with methane at temperatures selected within the range of about 500° to about 1000° C. The term "reducible" is used to identify those oxides of metals which are reduced by the methane contact. The term "oxide(s) of metal(s)" includes: (1) one or more metal oxides (i.e., compounds described by the general formula $M_xO_y$ wherein M is a metal, O is oxygen, and the subscripts x and y designate the relative atomic proportions of metal and oxide in the composition); and/or (2) one or more oxygen-containing metal compounds; provided that such oxides and compounds have the capability of performing to produce higher hydrocarbon products as set forth herein.

The preferred agents comprise reducible oxides of metals selected from the group consisting of manganese, tin, indium, germanium, antimony, lead, bismuth, and mixtures thereof. The particularly preferred agents comprise reducible oxides of manganese and mixtures of reducible oxides of manganese with other agents.

An important feature of the present invention is the precalcination of the hydroxylated magnesia support prior to addition of the at least one metal. The hydroxylated magnesia is preferably derived from magnesium hydroxide, e.g., magnesia produced from sea water. One such suitable magnesia is commercially available from CRI Industries as MgO-700.

Alternatively, the hydroxylated magnesia may be derived from sources other than magnesium hydroxide such as a magnesium-containing component contacted with hydroxyl-containing material (e.g., one or more compounds including hydroxyl groups). Such hydroxyl-containing materials include sodium hydroxide, potassium hydroxide, lithium hydroxide, slaked lime, calcium hydroxide, and hydroxides of barium. One method of producing the present hydroxylated magnesia comprises contacting a magnesium-containing component with (a) water for an extended period or (b) boiling water. Any suitable magnesium-containing component may be employed to produce hydroxylated magnesia. Examples include magnesia, magnesium chloride, and magnesium salts.

The hydroxylated magnesia is calcined prior to addition of the at least one metal at elevated temperatures in an oxygen-containing gas. The particular precalcining temperature will vary, but preferably it will be between about 300 and about 1200° C.

The contact agent can be prepared by any suitable method. Conventional methods such as precipitation, coprecipitation, impregnation or granulation can be used. Substantially any compound of manganese, tin, indium, germanium, antimony, lead, bismuth, and mixtures thereof can be employed in the preparation of the contact agent.

The preferred contact agent of this invention contains, in addition to the foregoing elements, at least one alkali metal. Sodium and/or compounds thereof are a particularly preferred alkali metal component. The atomic ratio in which these materials are combined to form the contact agent is not narrowly critical. However, the preferred atomic ratio of the reducible oxide component (expressed as the metal, e.g., Mn) to the alkali metal component (expressed as the metal, e.g., Na) is within the range of about 0.1:1 to about 100:1, more preferably within the range of about 0.3:1 to about 10:1.

Suitable metal compounds useful for impregnation include the acetates, acetylacetonates, oxides, carbides, carbonates, hydroxides, formates, oxalates, nitrates, phosphates, sulfates, tartrates, fluorides, chlorides, bromides or iodides.

After impregnation, the resulting composite is dried in an oven to remove solvent and the dried solid is prepared for use by calcining at elevated temperatures in an oxygen-containing gas (e.g., air) prior to use in the process of this invention. Particular calcination temperatures will vary, depending upon the particular metal compound or compounds employed. Preferably, the air temperature is selected within the range of about 300° to about 1200° C.

In addition to methane, the preferred feedstock employed in the method of this invention may contain other hydrocarbon or non-hydrocarbon components, although the methane content should typically be within the range of about 40 to about 100 volume percent, preferably about 80 to about 100 volume percent, more preferably about 90 to about 100 volume percent.

Operating temperatures for contacting the methane with the contact agent are preferably selected within the range of about 500° to about 1000° C.; the particular temperature selected depending upon the particular reducible metal oxides employed in the contact agent. For example, reducible oxides of certain metals may require operating temperatures below the upper part of the recited range to minimize sublimation or volatilization of the metals (or compounds thereof) during methane contact. Examples include reducible oxides of indium, germanium and bismuth (operating temperatures will preferably not exceed about 850° C.).

Operating pressures for the methane contacting step are not critical to the presently claimed invention. However, both general system pressure and partial pressure of methane have been found to affect overall results. Preferred operating pressures are within the range of about 1 to about 30 atmospheres.

Contacting methane with a contact agent to form higher hydrocarbons from methane also produces reduced metal oxides and water. The exact nature of the reduced metal oxides is unknown, and so is referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to about 1200° C.; the particular temperature selected depending on the metal(s) included in the contact agent.

In carrying out the present process, a single reactor apparatus containing a fixed bed of solids may be used with intermittent or pulsed flow of a first gas comprising methane followed by intermittent or pulsed flow of a second gas comprising oxygen (e.g., oxygen, oxygen diluted with an inert gas, or air, preferably air). The methane contacting step and the oxygen contacting step may also be performed in physically separate zones with solids recirculating between the two zones.

Thus, a suitable method for synthesizing hydrocarbons from a methane source comprises: (a) contacting a gas comprising methane and particles comprising a contact agent to form higher hydrocarbon products, water and reduced metal oxide; (b) removing particles comprising reduced metal oxide from the first zone and contacting the reduced particles in a second zone with an oxygen-containing gas to form particles comprising a contact agent; and (c) returning the particles produced in the second zone to the first zone. The steps are preferably repeated at least periodically, and more preferably the steps are continuous. In the more preferred embodiment, solids are continuously circulated between at least one methane contact zone and at least one oxygen contact zone.

Particles comprising a contact agent which are contacted with methane may be maintained as fluidized, ebullating, or entrained beds of solids. Preferably, methane is contacted with a fluidized bed of solids.

Similarly, particles comprising reduced metal oxide which are contacted with oxygen may be maintained as fluidized, ebullating, or entrained beds of solids. Preferably, oxygen is contacted with a fluidized bed of solids.

In the more preferred embodiment of the present invention, methane feedstock and particles comprising a contact agent are continuously introduced into a methane contact zone maintained at synthesizing conditions. Synthesizing conditions include the temperatures and pressures described above. Gaseous reaction products from the methane contact zone (separated from entrained solid) are further processed (e.g., passed through a fractionating system wherein the desired hydrocarbon products are separated from unconverted methane and combustion products). Unconverted methane may be recovered and recycled to the methane contact zone.

Particles comprising reduced metal oxide are contacted with oxygen in an oxygen contact zone for a time sufficient to oxidize at least a portion of the reduced oxide to produce a reducible metal oxide and to remove (i.e., combust) at least a portion of any carbonaceous deposit which may form on the particles in the methane contact zone. The conditions of the oxygen contact zone will preferably include a temperature selected within the range of about 300° to about 1200° C., pressures of up to about 30 atmospheres, and average particle contact time within the range of about 1 to about 120 minutes. Sufficient oxygen is preferably provided to oxidize all reduced metal oxide to produce a reducible oxide and to completely combust any carbonaceous deposit material deposited on the particles. At least a portion of the particles comprising the contact agent which are produced in the oxygen contact zone are returned to the methane contact zone.

The rate of solids withdrawal from the methane contact zone is desirably balanced with the rate of solids passing from the oxygen contact zone to the methane contact zone so as to maintain a substantially constant inventory of particles in the methane contact zone, thereby enabling steady-state operation of the synthesizing system.

The present invention is further illustrated by reference to the following Examples.

Methane contact runs were made at about atmospheric pressure in quartz tube reactors (12 mm. inside diameter) partially packed with 10 ml. of contact solids. The reactors were brought up to temperature under a flow of heated nitrogen which was switched to methane at the start of the run. Unless otherwise indicated, all methane contact runs described in the following Examples had a duration of two minutes. At the end of each methane contact run, the reactor was flushed with nitrogen and the solids were regenerated under a flow of air (usually at 800° C. for 30 minutes). The reactor was then again flushed with nitrogen and the cycle repeated. Most of the results reported below are based on the cumulative samples collected after the contact solids were "equilibrated"; i.e., after the aberrant characteristics of the fresh contact solid had dissipated. This allows more meaningful comparison between the contact solids within the scope of the present invention and other contact solids. Three to six cycles of methane contact and regeneration are generally sufficient to equilibrate the contact solid.

Space velocities are reported as gas hourly space velocities (hr.$^{-1}$) and are identified as "GHSV" in the Examples.

EXAMPLE I

Magnesium chloride was dissolved in water and hydrolyzed with aqueous sodium hydroxide. The magnesium hydroxide precipitate that formed was collected by filtration, washed with water, dried at 110° C. and then calcined at 500° C. in air for 16 hours. This calcined magnesium hydroxide support was impregnated with aqueous sodium permanganate to a 13 percent loading of the permanganate and then calcined at 1000° C. in air for 16 hours. The contact agent composition contained 5 weight percent manganese and 2.1 weight percent sodium on magnesia. The contact agent was run in the methane conversion process to yield the results shown in Table 1 below.

TABLE 1

| °C. | GHSV hr$^{-1}$ | % Conv | \multicolumn{7}{c}{Selectivity} |
|---|---|---|---|---|---|---|---|---|---|
| | | | $C_2=$ | $C_2$ | $C_3$ | $C_{4-7}$ | CO | $CO_2$ | Coke |
| 825 | 1200 | 23.8 | 33.1 | 15.0 | 5.8 | 4.3 | 1.5 | 40.2 | 0 |
| 850 | 1200 | 28.2 | 28.4 | 12.6 | 4.9 | 3.5 | 4.3 | 46.2 | 0 |

TABLE 1-continued

| °C. | GHSV hr$^{-1}$ | % Conv | \multicolumn{7}{c}{Selectivity} |
|---|---|---|---|---|---|---|---|---|---|
| | | | $C_2=$ | $C_2$ | $C_3$ | $C_{4-7}$ | CO | $CO_2$ | Coke |
| 825 | 600 | 42.5 | 26.6 | 9.2 | 4.7 | 14.9 | 0 | 44.4 | 0 |

EXAMPLE II

Magnesium chloride was dissolved in water and hydrolyzed with aqueous sodium hydroxide. The precipitate that formed was collected by filtration, washed with water and dried at 110° C. This dried magnesium hydroxide cake was impregnated with aqueous sodium permanganate to a 13 percent loading of the permanganate and calcined at 1000° C. in air for 16 hours. The contact agent composition contained 5 weight percent manganese and 2.1 weight percent sodium on magnesia. The contact agent was run in the methane conversion process to yield the results shown in Table 2 below.

TABLE 2

| °C. | GHSV hr$^{-1}$ | % Conv | \multicolumn{7}{c}{Selectivity} |
|---|---|---|---|---|---|---|---|---|---|
| | | | $C_2=$ | $C_2$ | $C_3$ | $C_{4-7}$ | CO | $CO_2$ | Coke |
| 825 | 1200 | 23.1 | 11.5 | 12.7 | 1.7 | .7 | 0 | 70.4 | 2.9 |
| 825 | 600 | 36.5 | 14.1 | 10.0 | 2.2 | .7 | 0 | 72.9 | 6.6 |

EXAMPLE III

The procedure of Example I was repeated, except that magnesium acetate was substituted for magnesium chloride. The results of the methane runs are shown in Table 3 below.

TABLE 3

| °C. | GHSV hr$^{-1}$ | % Conv | \multicolumn{7}{c}{Selectivity} |
|---|---|---|---|---|---|---|---|---|---|
| | | | $C_2=$ | $C_2$ | $C_3$ | $C_{4-7}$ | CO | $CO_2$ | Coke |
| 825 | 1200 | 10.5 | 38.0 | 38.0 | 5.7 | 3.8 | 0 | 13.6 | .8 |
| 850 | 1200 | 11.6 | 34.4 | 28.0 | 5.2 | 2.9 | 0 | 27.9 | 1.6 |
| 825 | 600 | 16.7 | 43.5 | 34.0 | 6.3 | 4.2 | 0 | 11.4 | .6 |

EXAMPLE IV

Magnesium acetate was calcined at 450° C. in air for 16 hours to yield magnesium oxide. This calcined magnesium oxide was impregnated with aqueous sodium permanganate to a 13 percent loading of permanganate and calcined at 1000° C. in air for 16 hours. The contact agent composition contained 5 weight percent manganese and 2.1 weight percent sodium on magnesia. The contact agent was run in the methane conversion process to yield the results shown in Table 4 below.

TABLE 4

| Temp °C. | GHSV hr$^{-1}$ | % Conversion | % $C_2$ + Selectivity |
|---|---|---|---|
| 800 | 600 | 32.5 | 27.5 |
| 825 | 600 | 36.0 | 21.0 |
| 825 | 1200 | 22.0 | 18.0 |

What is claimed is:

1. In an improved method for converting methane to higher hydrocarbons which comprises contacting a gas comprising methane with a contact agent comprising: (a) at least one reducible oxide of at least one metal, which oxide when with methane at a temperature within the range of about 500° to 1000° C. is reduced and produces higher hydrocarbon products and water, and (b) a support comprising a magnesia derived from magnesium hydroxide or from a magnesium-containing component contacted with hydroxyl-containing material; the improvement which comprises employing a contact agent wherein said support has been calcined prior to the addition of said reducible metal oxide.

2. The method of claim 1 wherein said reducible oxide is selected from the group consisting of manganese, tin, indium, germanium, antimony, lead, bismuth, and mixtures thereof.

3. The method of claim 1 wherein said hydrocarbon to be converted is in the form of a gas comprising methane.

4. The method of claim 3 wherein said gas comprising methane contains about 40 to about 100 volume percent methane.

5. The method of claim 4 wherein said gas comprising methane contains about 80 to about 100 volume percent methane.

6. The method of claim 5 wherein said gas comprising methane contains about 90 to about 100 volume percent methane.

7. The method of claim 1 wherein said agent comprises additionally at least one alkali metal.

8. The method of claim 7 wherein said alkali metal is selected from the group consisting of lithium, sodium, potassium, rubidium, cesium, and mixtures thereof.

9. The method of claim 7 wherein said alkali metal is selected from the group consisting of sodium, sodium compounds, and mixtures thereof.

10. The method of claim 1 wherein said magnesia is derived from magnesium hydroxide.

11. The method of claim 1 wherein said magnesia is derived from a magnesium-containing component contacted with hydroxyl-containing material.

12. The method of claim 1 wherein said support has been calcined at a temperature of about 300° to about 1200° C.

13. The method of claim 11 wherein said magnesium-containing component comprises magnesium chloride.

14. The method of claim 11 wherein said hydroxyl-containing material comprises water.

15. The method of claim 11 wherein said hydroxyl-containing material comprises boiling water.

* * * * *